United States Patent
Kono et al.

(10) Patent No.: US 11,866,483 B2
(45) Date of Patent: Jan. 9, 2024

(54) FIBROSIS-INHIBITING COMPOSITION, CELLS PRODUCING SAME, AND CELL SHEET COMPRISING SAID CELLS

(71) Applicants: KanonCure, Inc., Yonago (JP); National University Corporation Tottori University, Tottorishi (JP)

(72) Inventors: Yohei Kono, Yonago (JP); Noriko Itaba, Tottorishi (JP); Goshi Shiota, Tottorishi (JP)

(73) Assignees: KanonCure, Inc., Yonago (JP); National University Corporation Tottori University, Tottori (JP)

( * ) Notice: Subject to any disclaimer, the term of this patent is extended or adjusted under 35 U.S.C. 154(b) by 163 days.

(21) Appl. No.: 16/972,285

(22) PCT Filed: May 30, 2019

(86) PCT No.: PCT/JP2019/021603
§ 371 (c)(1),
(2) Date: Dec. 4, 2020

(87) PCT Pub. No.: WO2019/235362
PCT Pub. Date: Dec. 12, 2019

(65) Prior Publication Data
US 2021/0115112 A1    Apr. 22, 2021

(30) Foreign Application Priority Data
Jun. 8, 2018  (JP) .................................. 2018-110587

(51) Int. Cl.
| | | |
|---|---|---|
| A61K 38/00 | (2006.01) | |
| C07K 14/81 | (2006.01) | |
| C12N 5/0775 | (2010.01) | |
| A61K 35/28 | (2015.01) | |

(52) U.S. Cl.
CPC .......... *C07K 14/8146* (2013.01); *A61K 35/28* (2013.01); *C12N 5/0663* (2013.01); *A61K 38/00* (2013.01)

(58) Field of Classification Search
CPC .... C07K 14/8146; A61K 35/28; A61K 38/00; C12N 5/0663
See application file for complete search history.

(56) References Cited

U.S. PATENT DOCUMENTS

| | | |
|---|---|---|
| 9,555,061 B2 | 1/2017 | Shiota et al. |
| 10,597,398 B2 | 3/2020 | Shiota et al. |
| 2004/0109870 A1 | 6/2004 | Yodoi et al. |
| 2008/0166329 A1 | 7/2008 | Sung et al. |
| 2012/0052524 A1 | 3/2012 | Kinooka et al. |
| 2014/0112892 A1 | 4/2014 | Shiota et al. |
| 2017/0216362 A1 | 8/2017 | Oka et al. |
| 2018/0028536 A1 | 2/2018 | Shiota et al. |
| 2019/0055249 A1 | 2/2019 | Shiota et al. |
| 2020/0190476 A1 | 6/2020 | Shiota et al. |

FOREIGN PATENT DOCUMENTS

| | | |
|---|---|---|
| CN | 104225681 A | 12/2014 |
| EP | 2698365 A1 | 2/2014 |
| JP | 2004-67542 A | 3/2004 |
| WO | WO-2012/141038 A1 | 10/2012 |
| WO | WO-2015/147107 A1 | 10/2015 |
| WO | WO-2016/068217 A1 | 5/2016 |
| WO | WO-2017/047762 A1 | 3/2017 |
| WO | WO-2019/044753 A1 | 3/2019 |
| WO | WO-2019/235362 A1 | 12/2019 |

OTHER PUBLICATIONS

An et al., "Milk fat globule-EGF factor 8, secreted by mesenchymal stem cells, protects against liver fibrosis in mice," Gastroenterology 152(5):1174-1186 (2017).
Iimuro et al., "Special edition, Organ fibrosis and its control, Gene therapy for liver fibrosis," "4. Treatment of hepatic fibrosis with MMP-1," Medical Science Digest 29(10):404-407 (2003).
International Search Report and Written Opinion dated Sep. 3, 2019, for PCT International Application No. PCT/JP2019/021603, Kono et al., "Fibrosis-Inhibiting Composition, Cells Producing Same, and Cell Sheet Comprising said Cells," filed May 30, 2019 (11 pages).
Itaba et al., "Reversal of established liver fibrosis by IC-2-engineered mesenchymal stem cell sheets," Sci. Rep. 9(1):6841 (2019) (12 pages).
Itaba et al., "Science of mesenchymal stem cell differentiation sheet aiming at clinical application to liver cirrhosis: Analysis of the mechanism in action," Programs and abstracts of the 25th Japanese Society for the Research of Hepatic Cells S2-7: 34 (2018).
Kouno et al., "Hepatic fibrosis inhibitory effect of human mesenchymal stem cell hepatocyte sheet transplantation," 22nd Japanese Society for the Research of Hepatic Cells. 63: P4-5 (2015) (Abstract) (2 pages).
Noble et al., "Pirfenidone in patients with idiopathic pulmonary fibrosis (Capacity): two randomised trials," Lancet 377(9779):1760-1769 (2011).
Shimizu et al., "All-trans retinoic acid ameliorates hepatic stellate cell activation via suppression of thioredoxin interacting protein expression," J. Cell Physiol. 233(1):607-616 (2018).

(Continued)

*Primary Examiner* — Jeanette M Lieb
(74) *Attorney, Agent, or Firm* — Clark & Elbing LLP; Susan M. Michaud

(57) ABSTRACT

[Problem] To provide a composition and a cell sheet which are highly effective for inhibiting fibrosis, or cells having fibrosis-inhibiting activity, which are useful in regenerative medicine. [Solution] A medium containing IC-2 or a related compound is inoculated with mesenchymal stem cells or bone marrow mononuclear cells, and the cells are cultured for a prescribed period of time while the IC-2 or related compound is maintained at a constant concentration, thereby allowing a composition and a cell sheet which are highly effective for inhibiting fibrosis, or cultured cells having fibrosis-inhibiting activity, to be obtained.

6 Claims, 2 Drawing Sheets

(56) References Cited

OTHER PUBLICATIONS

Yokoo et al., "Suppression of hepatic fibrosis by MMP13 gene transfer," Lecture abstracts of the 52nd Annual Meeting of Japan Society of Hepatology, Kanzo 57: S1, Abstract 240 #0-165 (2016) (2 pages).
Du et al., "Transplantation of human matrix metalloproteinase-1 gene-modified bone marrow-derived mesenchymal stem cell attenuates CCL4-induced liver fibrosis in rats," Int. J. Mol. Med. 41(6):3175-3184 (2018).
Iimuro et al., "Delivery of matrix metalloproteinase-1 attenuates established liver fibrosis in the rat," Gastroenterology 124(2):445-458 (2003).
Itaba et al., "Identification of the small molecule compound which induces hepatic differentiation of human mesenchymal stem cells," Regen. Ther. 2:32-41 (2015).
Okuyama et al., "Overexpression of thioredoxin prevents thioacetamide-induced hepatic fibrosis in mice," J. Hepatol. 42(1):117-123 (2005).
Partial Supplementary European Search Report dated Apr. 7, 2022, for European Application No. 19815672.1, Kono et al., "Fibrosis-Inhibiting Composition, Cells Producing Same, and Cell Sheet Comprising said Cells," filed May 30, 2019 (16 pages).
Extended European Search Report dated Jul. 8, 2022, for European Application No. 19815672.1, KanonCure, Inc., et al., "Fibrosis-Inhibiting Composition, Cells Producing Same, and Cell Sheet Comprising Said Cells," filed May 30, 2019 (20 pages).
Akimoto et al., "Facile Cell Sheet Manipulation and Transplantation by Using in Situ Gelation Method," J Biomed Mater Res B Appl Biomater. 102(8):1659-68 (2014).
Dong et al., "The anti-fibrotic effects of mesenchymal stem cells on irradiated lungs via stimulating endogenous secretion of HGF and PGE2," Sci Rep. 5:8713 (2015) (10 pages).
Extended European Search Report dated Dec. 23, 2020, for European Patent Application No. 18851336.0, Itaba et al., "Cell Sheet Having Fibrosis Inhibitory Action," filed Aug. 27, 2018 (13 pages).
English translation of International Search Report and Written Opinion for International Application No. PCT/JP2018/031537, dated Nov. 20, 2018 (9 pages).
Itaba et al., "Hepatic fibrosis inhibitory action by bone marrow-derived mesenchymal stem cell hepatocyte sheet", Programs and abstracts of the 23rd Japanese Society for the Research of Hepatic Cells. 65:P7-1 (2016) (Abstract only) (2 pages).
Itaba et al., "Hepatic fibrosis inhibitory action of human mesenchymal stem cell hepatocyte sheet", Regenerative Medicine and Tissue Engineering. 16:325:O-41-5 (2017) (Abstract only) (3 pages).
Itaba et al., "Hepatic fibrosis inhibitory effect of mesenchymal stem cell-derived hepatocyte sheet," Kanzo. 58(Suppl 1):A411:0-424 (Apr. 2017) (Abstract only) (3 pages).
Itaba et al., "Human Mesenchymal Stem Cell-Engineered Hepatic Cell Sheets Accelerate Liver Regeneration in Mice," Sci Rep. 5:16169 (2015) (17 pages).
Kouno et al., "Effect of liver disease therapeutic cell sheet on repairing tissue with respect to hepatic fibrosis pathology," Programs and abstracts of the 24th Annual Meeting of the Japanese Society for the Research of Hepatic Cells. 46:06-2 (2017) (Abstract only) (2 pages).
Kouno et al., "Review on anti-fibrosis action by human mesenchymal stem cell hepatocyte sheet and mechanism of anti-fibrosis action," Kanzo. 57(Suppl 1): A242:0-169 (2016) (Abstract only) (3 pages).
Kouno et al., "Therapeutic effect of mesenchymal stem cell hepatocyte sheet on hepatic fibrosis model, and action mechanism", Regenerative Medicine and Tissue Engineering. 15:242:0-29-5 (2016) (Abstract only) (3 pages).
Lozito et al., "Human mesenchymal stem cells generate a distinct pericellular zone of MMP activities via binding of MMPs and secretion of high levels of TIMPs," Matrix Biol. 34:132-43 (2014).
Shiota et al., "Progress in Stem Cell-Based Therapy for Liver Disease," Hepatol Res. 47(2):127- 141 (Feb. 2017).
Office Action dated Aug. 29, 2023 for Japanese Patent Application No. 2022-163505, Shiota et al., "Cell Sheet Having Fibrosis Inhibitory Action," filed Oct. 11, 2022 (English translation) (5 pages).

_US 11,866,483 B2_

FIBROSIS-INHIBITING COMPOSITION, CELLS PRODUCING SAME, AND CELL SHEET COMPRISING SAID CELLS

FIELD OF THE INVENTION

The present disclosure relates to a cell sheet used in regenerative medicine. Specifically, the present disclosure relates to a cell sheet having increased fibrosis inhibitory activity. In addition, the present disclosure also relates to a composition containing a matrix metalloprotease (MMP) family protein(s).

BACKGROUND OF THE INVENTION

"Regenerative medicine" uses cells, which grow through, for instance, culturing, to allow for treatment by which not only the functions but also the structure of the body is restored to an original state or a state as close to the original state as possible. Although there is a method in which cultured cells are injected as they are, grafted cells have to be able to integrate into a tissue for colonization to utilize the repair function of cells in a given tissue.

Cell sheets are prepared by culturing cells collected from a patient's tissue or an established cell line to form a sheet in which a certain number of cells grown by culturing are adhered to each other to form a monolayer sheet. A lower portion of the cell sheet has adhesion proteins such as extracellular matrix. Accordingly, the cell sheet can be engrafted in a transplanted tissue without surgical stitching. The engrafted cell sheet can release a humoral factor, which promotes regeneration and healing. To date, transplantation to and regenerative treatment of human cornea, heart, esophagus, and so on have been implemented. The scope of application should be increasingly extended in the future.

The present inventors have reported that a compound with Wnt/β-catenin signal inhibitory activity was used to differentiate mesenchymal stem cells and bone marrow-derived mononuclear cells into cells with a liver function; the differentiated cells were formed as a sheet; and a plurality of the sheets were layered and used to suppress hepatic injury in mice (Patent Literature 1). Patent Literature 1 reports a composite mechanism of C3-induced NF-kB/IL-6/STAT3 activation, thioredoxin (TRX)-induced TRX oxidation and reduction cycle activation, and amphiregulin-induced EGFR pathway activation.

Tissue fibrosis is an example of a symptom of hepatic injury. The fibrosis in the liver progresses into hepatic cirrhosis and/or liver cancer. In addition, the fibrosis may occur in, for instance, the lung, kidney, heart and skin. Non Patent Literature 1 describes the results of a clinical trial of pirfenidone in the treatment of fibrosis.

In this connection, the present inventors have discovered a method allowing for increased fibrosis inhibitory activity in a cell sheet made of bone marrow mononuclear cells, which is described in a co-pending application PCT/JP2018/031537 (claiming a priority from Japanese Patent Application No. 2017-168118 and published as WO2019/044753 A1 on Mar. 7, 2019, and therefore not regarded as a prior art literature for the present application). Specifically, it discloses that a cell sheet of bone marrow mononuclear cells with increased MMP-1 and MMP-14 activities was prepared by increasing the seeding density at the time of preparing the sheet.

PRIOR ART REFERENCES

Patent Literature

Patent Literature 1: WO 2012/141038 A1

Non Patent Literature

Non Patent Literature 1: Nobel et al., Lancet. May 21; 377(9779): 1760-9

SUMMARY OF THE INVENTION

Problem to be Solved by the Invention

As described above, establishment of a regenerative medicine treatment protocol without any adverse effect, in particular, a treatment protocol using a cell sheet is in progress. However, such treatment using a cell sheet requires laparotomy or an operation using an endoscope. Thus, it is desired to develop a composition or a treatment protocol that can be used to effectively treat liver dysfunction or fibrosis in various organs.

Further, regarding conventional cell sheets, it is necessary to attach a plurality of the cell sheets onto the lesion area. On top of that, in generating a differentiated cell sheet, it is difficult to strictly manage and determine the number of differentiated cells in all sheets. Consequently, it is cumbersome to manage the above cell sheet as a product. Hence, in the cell sheet treatments, there is still a need for increasing the efficacy of a single cell sheet, namely for increasing activity of therapeutically effective factors, etc.

Means to Solve the Problem

The present inventors have conducted intensive research to solve the above problems and, as a result, have succeeded in obtaining, by a step of culturing mesenchymal stem cells or bone marrow mononuclear cells, a composition containing matrix metalloprotease (MMP) family proteins having fiber-degrading activity and/or a hepatic stellate cell activation inhibitor, a cell that can produce such a composition and a cell sheet made of such cells. Because the inventive composition comprises multiple kinds of MMPs and/or hepatic stellate cell activation inhibitors such as TRX and/or MFGE-8, the composition makes it possible to enhance in vivo the fibrosis inhibitory effect through additive mechanism.

Moreover, because the cell sheet obtained by the above step can produce the aforementioned composition, the cell sheet should be the one that has higher capability to produce and release inhibitory factors for fibrosis.

Accordingly, the present invention encompasses the following aspects.

[1] A composition for inhibiting fibrosis comprising matrix metalloprotease family members having fiber-degrading activity and a hepatic stellate cell activation inhibitor;

[2] The composition for inhibiting fibrosis according to [1], wherein the matrix metalloprotease having fiber-degrading activity is MMP-1, MMP-14, MMP-2 or MMP-13, or any combination thereof;

[3] The composition for inhibiting fibrosis according to [1], wherein the hepatic stellate cell activation inhibitor is thioredoxin (TRX);

[4] The composition for inhibiting fibrosis according to [1], wherein the matrix metalloproteases having fiber-degrading activity are MMP-1, MMP-14, MMP-2 and MMP-13, and the hepatic stellate cell activation inhibitor is thioredoxin (TRX);

[5] A composition for inhibiting fibrosis which is produced by a bone marrow mononuclear cell or a mesenchymal stem cell and comprises larger amounts of matrix metalloproteases having fiber-degrading activity and a hepatic stellate cell activation inhibitor in said cell and/or secreted products thereof;

[6] The composition for inhibiting fibrosis according to [5], which is produced by a bone marrow mononuclear cell or a mesenchymal stem cell and comprises larger amounts of matrix metalloproteases having fiber-degrading activity and a hepatic stellate cell activation inhibitor in said cell and/or secreted products thereof, wherein the matrix metalloproteases comprise larger amounts of matrix metalloproteases having particularly high collagen-degrading activity;

[7] The composition for inhibiting fibrosis according to [6], wherein the matrix metalloproteases having the fiber-degrading activity comprise larger amount of MMP-1 and MMP-14 as the matrix metalloproteases having particularly high collagen-degrading activity;

[8] A mesenchymal stem cell that produces the composition for inhibiting fibrosis according to any of the aforementioned;

[9] A method of producing a composition having high fibrosis inhibitory effect comprising the steps of:
  i) culturing bone marrow mononuclear cells or mesenchymal stem cells in a culture medium containing IC-2 or an analogous compound thereof;
  ii) collecting cultured cells, secreted products of the cells or both from the culture obtained in the step i); and
  iii) recovering proteins from the cultured cells, the secreted products of the cells or both collected in the step ii);

[10] The method according to [9], wherein the compound used in the step of culturing bone marrow mononuclear cells or mesenchymal stem cells in the culture medium containing IC-2 or the analogous compound thereof is represented by the following formula (1):

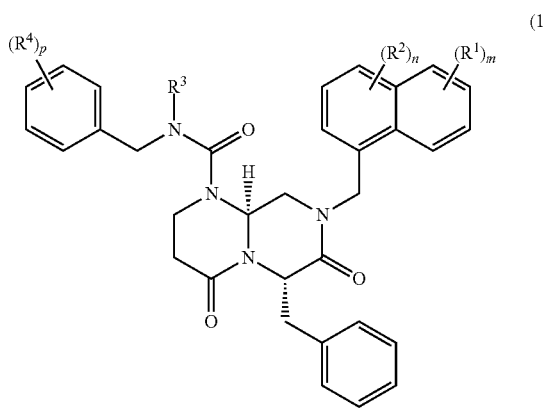

wherein $R^1$, $R^2$ and $R^4$ are the same or different and each represents H, halogen, nitro, cyano, OH, optionally substituted C1-C6 alkyl, optionally substituted C2-C6 alkenyl, optionally substituted C1-C6 alkoxy, aryl or heteroaryl;

$R^3$ is H, optionally substituted C1-C6 alkyl or optionally substituted C2-C6 alkenyl;

m is an integer from 1 to 4;

n is an integer from 1 to 3; and p is an integer from 1 to 5, provided that N-[(5-methyl-2-furyl)methylideneamino]-2-phenoxy-benzamide is excluded;

[11] A method of producing a cell sheet having high fibrosis inhibitory effect comprising the steps of:
  i) culturing mesenchymal stem cells in a culture medium containing IC-2 or an analogous compound thereof for at least 9 days characterized in that concentration of IC-2 or the analogous compound thereof is maintained constant throughout the cultivation; and
  ii) collecting a cell sheet containing the mesenchymal stem cells and secreted products of said cells generated in the step i);

[12] The method according to [11], wherein IC-2 or the analogous compound thereof is represented by the following formula (1):

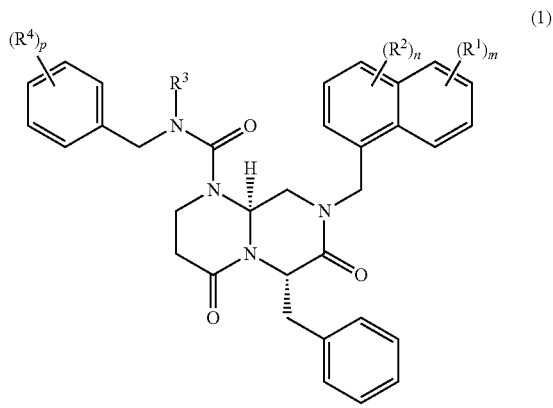

wherein $R^1$, $R^2$ and $R^4$ are the same or different and each represents H, halogen, nitro, cyano, OH, optionally substituted C1-C6 alkyl, optionally substituted C2-C6 alkenyl, optionally substituted C1-C6 alkoxy, aryl or heteroaryl;

$R^3$ is H, optionally substituted C1-C6 alkyl or optionally substituted C2-C6 alkenyl;

m is an integer from 1 to 4;

n is an integer from 1 to 3; and p is an integer from 1 to 5, provided that N-[(5-methyl-2-furyl)methylideneamino]-2-phenoxy-benzamide is excluded;

[13] A method for increasing production of a fibrosis inhibitor by a mesenchymal stem cell comprising culturing bone marrow mononuclear cells or mesenchymal stem cells in a culture medium containing IC-2 or an analogous compound thereof; and

[14] The method according to [13], wherein IC-2 or the analogous compound thereof is represented by the following formula (1):

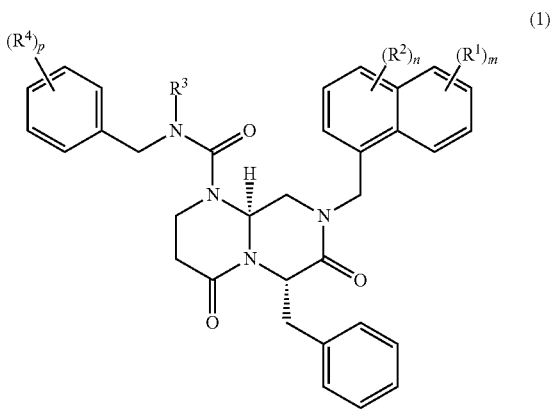

(1)

wherein $R^1$, $R^2$ and $R^4$ are the same or different and each represents H, halogen, nitro, cyano, OH, optionally substituted C1-C6 alkyl, optionally substituted C2-C6 alkenyl, optionally substituted C1-C6 alkoxy, aryl or heteroaryl;

$R^3$ is H, optionally substituted C1-C6 alkyl or optionally substituted C2-C6 alkenyl;

m is an integer from 1 to 4;
n is an integer from 1 to 3; and
p is an integer from 1 to 5,
provided that N-[(5-methyl-2-furyl)methylideneamino]-2-phenoxy-benzamide is excluded.

Effects of the Invention

The composition obtained by the present invention comprises various MMPs, and also comprises TRX and/or MFGE-8 which are hepatic stellate cell activation inhibitors. Moreover, the cells or the cell sheets obtained by the present invention are highly capable of producing and releasing various proteins that can be factors with an inhibitory effect on fibrosis. Thus, the disclosed cell sheet is considered to have a higher fibrosis inhibitory effect than that of conventional ones. In particular, the cell sheet of the present invention has a high ability to suppress fibrosis in various organs including the liver. Such a cell sheet has been for the first time discovered using the method of producing a cell sheet according to this disclosure.

The cell sheet obtained by the present invention is useful as a cell sheet for, in particular, liver disease treatment and for the treatment of organ fibrosis in other organs.

The disclosed cell sheet can produce various MMPs and hepatic stellate cell activation inhibitors. Especially, the cell sheet of the present invention can produce significant amounts of MMP-1, MMP-2, MMP-13 and MMP-14 as well as TRX. That is, it is possible to efficiently degrade various organ fibrosis-related collagens including type-I collagen and simultaneously suppress activation of hepatic stellate cells, thereby reducing fiber production by hepatic stellate cells. Such a composition and a cell sheet were not known in the past.

According to the present disclosure, a cell sheet having an increased inhibitory effect on fibrosis can be obtained.

DETAILED DESCRIPTION OF THE INVENTION

<Mesenchymal Stem Cell>

Figure 1:
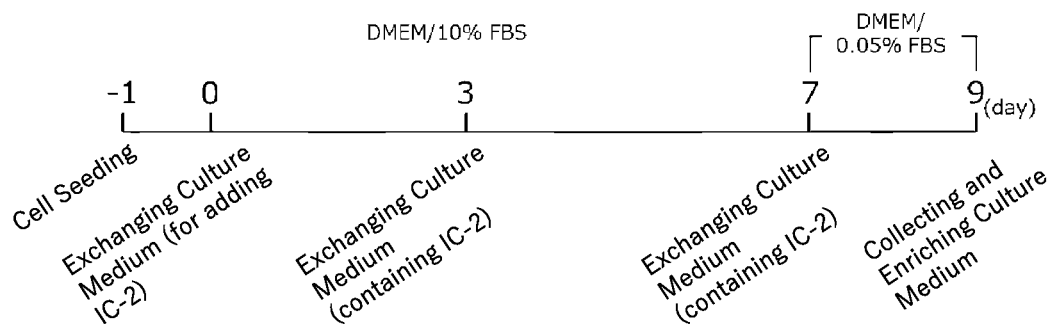
FIG. 1 illustrates an embodiment of a method for producing a composition for inhibiting fibrosis, cells that produce said composition and a cell sheet comprising said cells according to the present invention.

The cell sheet of the present disclosure may be produced from mesenchymal stem cells.

As used herein, the "mesenchymal stem cells" includes somatic stem cells derived from mesenchyme. The mesenchymal stem cells have an ability to differentiate into cells belonging to mesenchymal tissue. The mesenchymal stem cells are expected to be applicable to modern regenerative medicine such as restructuring of bone, blood vessel and myocardium.

Examples of the "mesenchymal stem cells" include bone marrow mesenchymal cells and umbilical cord blood-derived stem cells. The mesenchymal stem cells are presumed to be present in all tissues having mesenchymal tissue. Among the mesenchymal tissues, bone marrow mesenchymal stem cells can be easily collected by bone marrow aspiration and can be cultured by the established protocol. Although until recently the mesenchymal stem cells were reported to be present in bone marrow, it has now been shown that umbilical cord blood as well as bone marrow is a possible source of mesenchymal stem cells, suggesting applications of umbilical cord blood stem cells for tissue-engineering repair of bone and cartilage or for clinical regenerative medicine therapy. Meanwhile, mesenchymal stem cells generally have a short life span, and are relatively difficult to maintain in in vitro long-term culture. However, stably proliferating human bone marrow-derived and human umbilical cord blood-derived mesenchymal stem cell lines have already been established by introducing genes such as hTERT gene. While these cells stably proliferate, they have no chromosomal abnormality but have a functional contact inhibition. Besides, they do not form tumors when transplanted into immunosuppressed animals. Also, since they do not affect cellular differentiation, these cells are useful for research on differentiation of mesenchymal stem cell. Accordingly, any of the above mesenchymal stem cells or mesenchymal stem cell lines may be used in the present invention.

Evidence has suggested that bone marrow-derived stem cells play roles in both progression and regression of hepatic fibrosis. At the time of regression from $CCl_4$-induced hepatic fibrosis, the bone marrow-derived mesenchymal stem cells migrate to a fibrous liver portion, where they may express, for instance, matrix metalloprotease-13 (MMP-13) (Cheng Y J, et al., Life Sci., 2009; 85 (13-14): 517-525).

As such, the present invention makes it possible to enhance the fibrosis inhibitory activity possessed by the mesenchymal stem cells, which is intrinsically useful in the treatments of liver disease and fibrosis of organs.

<Bone Marrow Mononuclear Cells>

Currently, widely used mesenchymal stem cells are obtained by a method comprising seeding bone marrow mononuclear cells on a culture dish and collecting fibroblast-like colony-forming cells (CFU-F) emerged at 2 to 3 weeks after the start of culture. Accordingly, it is possible to utilize the bone marrow mononuclear cells for the production of a composition for inhibiting fibrosis, a cell producing said composition and a cell sheet comprising said cells of the present invention.

<Cell Sheet Comprising Mesenchymal Stem Cells or Bone Marrow Mononuclear Cells>

The cell sheet, which is one of the embodiments of the present invention, can be produced by exposing the cells to IC-2 or an analogous substance thereof during a step of making the sheet. The cells are cultured in a culture medium containing IC-2 or an analogous substance thereof for a specified period from the next day of seeding to obtain the cell sheet of the present invention. The culturing period of the cell sheet may be at least for 7 days, 8 days, 9 days, 10 days, 11 days or 12 days. The period of exposure to IC-2 or an analogous compound thereof may be at least for 7 days, 8 days, 9 days, 10 days, 11 days or 12 days. In order to avoid deterioration of the culture medium and to maintain a constant concentration of IC-2 or an analogous compound thereof in the culture medium during the above period, it is preferable to exchange the culture medium containing IC-2 or an analogous substance thereof every 3 days, or within 4 days.

When using the method of producing a cell sheet, which is one of the embodiments of the present invention, the supernatant of 9 days culture contains several times higher amounts of MMPs and TRX than those observed in usual culture. That is, it has been revealed that the cell sheet of the present invention has increased productivity of MMPs and TRX as compared to conventional sheets comprising mesenchymal stem cells. Accordingly, the cell sheet of the present invention typically comprises mesenchymal stem cells and extracellular matrix, and also significant amounts of MMPs and TRX that are the secreted products of the mesenchymal stem cells. Collectively, the cells and the cell sheet that can produce the inventive composition with liver fibrosis inhibitory effect can be not only used by themselves as products for regenerative medicine, but also are useful as cells and cell sheet for the production of MMPs and/or TRX.

<Matrix Metalloproteases (MMPs)>

As used herein, the matrix metalloproteases (MMPs) are a group of metalloprotease (general term of a protease having a metal ion at the active center) and each contains a zinc ion ($Zn^{2+}$) or a calcium ion ($Ca^{2+}$) at its active center. Various activities have been reported, including decomposition of extracellular matrix composed of collagen, proteoglycan, elastin and so on, degradation of proteins expressed on cell surface, and processing of biologically active substances. Enzymes belonging to the MMP family are classified in two types, i.e. a secreted type and a membrane-bound type. Secreted type MMP works at a site apart from the secretory cells. Membrane-bound type MMP is thought to be expressed on the cell surface.

An embodiment of the present invention provides a composition comprising MMP-1, MMP-2, MMP-13 and MMP-14, and TRX, and any combination thereof.

In the present invention, "MMP-1" is a secreted type MMP which is also referred to as interstitial collagenase. "MMP-2" is a secreted type MMP which is also referred to as gelatinase. "MMP-13" is a secreted type MMP which is also referred to as collagenase 3. These secreted type MMPs are secreted out from the cells as an inactive precursor enzyme and are then converted to an active form. "MMP-14" is a membrane-bound type MMP. MMP-14 is expressed on the cellular membrane and considered to be involved in the decomposition of extracellular matrix surrounding cells. The present inventors have surprisingly found that the culture supernatant of the cell sheet obtained by culturing mesenchymal stem cells for a specified period under the presence of IC-2 contained large amounts of MMP-1, MMP-2, MMP-13 and MMP-14, and TRX, and thereby arriving at the present invention. It was surprising that MMP-14, a membrane-bound type MMP, was present in the supernatant in a larger amount than in the control group.

<Hepatic Stellate Cell Growth and Activity Inhibitor>

The hepatic stellate cells store vitamin A and are located in the gap between hepatocytes and liver sinusoidal endothelium which is referred to as space of Disse. The hepatic stellate cells are activated and changed to myofibroblast-like form when the liver is damaged. The activated hepatic stellate cells promote liver regeneration by secreting cytokines such as HGF which are necessary for hepatocyte regeneration. On the other hand, the activated hepatic stellate cells have been known to be involved in liver fibrosis by producing collagens and TGF-β. The liver fibrosis is caused by differentiation of the hepatic stellate cells normally storing vitamin A into myofibroblast-like cells by various stimuli, leading to abnormal secretion of type-I collagen (Friedman S L (2008) Hepatic stellate cells: protean, multifunctional, and enigmatic cells of the liver. Physiological reviews 88(1): 125-172. doi: 10.1152/physrev. 00013. 2007). The hepatic stellate cell activation inhibitor is a factor to inhibit the activation of hepatic stellate cell. TRX and Milk fat globule EGF factor 8 (MFGE-8) have been reported as examples of such factors. Especially, even exogenous thioredoxin (TRX) has been reported to suppress hepatic stellate cell growth (JP 2004-067542 A).

An embodiment of the present invention relates to a mesenchymal stem cell or a bone marrow mononuclear cell capable of secreting large amounts of MMP-1, MMP-2, MMP-13 and MMP-14 as well as TRX, and a method of producing such cells. The mesenchymal stem cell or bone marrow mononuclear cell of the present invention can produce large amounts of these matrix metalloproteases and a hepatic stellate cell activation inhibitor TRX. This is considered to be attributable to the effect of IC-2 or the analogous compounds thereof and the effect of the disclosed method of producing the aforementioned cells.

Preparation of the cells of the present invention requires exposure of the cells to IC-2 or an analogous compound thereof for at least 7 days, 8 days, 9 days, 10 days, 11 days or 12 days with maintaining the concentration of the aforementioned compound above a certain level.

Specifically, the final concentration of IC-2 or the analogous compound thereof in the culture medium should preferably be maintained at any one of 20 μM, 15 μM, 10 μM, 5 μM or above. To maintain the concentration, it is preferable to exchange the medium with fresh medium containing the specified concentration of IC-2 or an analogous compound thereof every several days, preferably every 3 days or every 4 days.

The cells of the present invention have a significant inhibitory effect on fibrosis as described in Examples section below. The expression of a member of MMP family that promotes degradation of collagen (e.g. type-I collagen) excessively accumulated in organ fibrosis and the expression of a hepatic stellate cell activation inhibitor are the indication of the fibrosis inhibitory effect according to the present invention.

As used herein, "fibrosis inhibitory effect" is used as the same meaning as "fiber-degrading activity".

The composition for inhibiting fibrosis, the cell sheet and the cell of the present invention may be used for transplantation on the surface of the liver. However, since they are derived from a mesenchymal stem cell or bone marrow mononuclear cell, they are applicable to suppression of any tissue fibrosis, and therefore they may be systemically transplantable, for instance, subcutaneous transplantation. The composition for inhibiting fibrosis, the cell sheet or the cell of the present invention may be derived from autologous cells. However, even those derived from heterologous cells are expected to exert sufficient efficacy. Regarding the heterologous transplantation, because mesenchymal stem cells show suppression of transplantation immunity, the heterologous transplantation would be possible without using an immunosuppressant.

When the cell sheet of the present invention is grafted, the sheet may consist of a monolayer or multi-layers. Moreover, the number of the sites to be grafted may be one or more. When grafted to more than one site, they may be 2, 3, 4, 5, 6 or more sites, or may be within this range.

The composition for inhibiting fibrosis, the cell sheet and the cell of the present invention have a significant fibrosis inhibitory effect as compared to previously studied liver treatment technologies using mesenchymal stem cells. Especially, as demonstrated in the Examples section below, the composition for inhibiting fibrosis of the present invention contains, among other MMPs, the MMP-1 and MMP-13 that have collagenases activity in an amount several times higher than a cell sheet obtained by simply culturing mesenchymal stem cells. In addition, TRX is also produced in significantly larger amount than that in the control group.

<Method of Producing Composition for Inhibiting Fibrosis, Cell Sheet and Cells with Fibrosis Inhibitory Activity>

Mesenchymal stem cells are seeded on a temperature-responsive reaction plate containing a culture medium. Examples of the culture medium include bFGF-containing DMEM/10% FBS. The number of cells seeded is, for instance, $1.0 \times 10^3$ cells/cm². The number can be changed as appropriate depending on the size of a flask or the culturing conditions, which is within the scope of knowledge of those skilled in the art. While exchanging the culture medium every 3 days or every 4 days, the cells are cultured for at least 7 days in the presence of IC-2 or an analogous compound thereof at 37° C. and 5% $CO_2$. The mesenchymal stem cells or bone marrow mononuclear cells form sheet-like structure after cultivation for a certain period by intercellular adhesion.

<IC-2 and Analogous Compound Thereof>

In the present disclosure, IC-2 and analogous compounds thereof as used for culturing the cell sheet include those disclosed in JP 2011-219435 A, WO 2012/141038 A1, WO 2015/147107 A1, or WO 2017/047762 A1. The compounds described in these literatures are incorporated herein by reference.

Examples of the preferable compounds include IC-2 ((6S, 9aS)-6-phenyl-8-naphthalen-1-ylmethyl-4,7-dioxo-hexahydro-pyrazino[1,2-a] pyrimidine-1-carbocylic acid benzylamide) and derivatives thereof as described in WO 2012/141038 A1. Preferable examples include one or more compounds selected from the group consisting of the compounds of formula (1), a salt thereof and a solvate thereof:

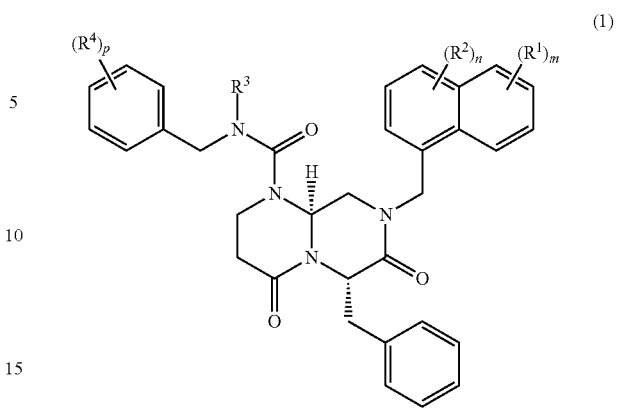

wherein $R^1$, $R^2$ and $R^4$ are the same or different and each represents H, halogen, nitro, cyano, OH, optionally substituted C1-C6 alkyl, optionally substituted C2-C6 alkenyl, optionally substituted C1-C6 alkoxy, aryl or heteroaryl;

$R^3$ is H, optionally substituted C1-C6 alkyl or optionally substituted C2-C6 alkenyl;

m is an integer from 1 to 4;

n is an integer from 1 to 3; and p is an integer from 1 to 5, provided that N-[(5-methyl-2-furyl)methylideneamino]-2-phenoxy-benzamide is excluded.

More preferable examples of IC-2 and analogous compounds thereof include a differentiation inducer comprising one or more compounds selected from the group consisting of the compounds of formula (1), a salt thereof and a solvate thereof.

The above compounds are given solely for the purpose of illustration. As long as a cell sheet or a composition containing MMPs and TRX of the present invention can be obtained, any derivatives of the above compounds are contemplated by the present invention.

<Determination of Fibrosis Inhibitory Effect>

Expression and production of MMP family members and TRX in cultured cells or the secreted products of those cells were determined by Western blotting and ELISA.

EXAMPLES

Hereinafter, the present invention will be further described by Examples. However, the present invention is not limited to them.

Example 1

Production of Cell Sheet

The following reagents, etc. were used to produce a cell sheet.

Cells: bone marrow-derived mesenchymal stem cell line, UE7T-13 cells.

Chemicals: 15 μM IC-2 (diluted with DMSO; the solution was used at the final concentration of 0.1% in the culture medium).

Culture medium: DMEM/10% FBS (Dulbecco's Modified Eagle's Medium (DMEM, Nissui Pharmaceutical Co., Ltd., Tokyo, Japan) containing inactivated fetal bovine serum (FBS; Nichirei Biosciences Inc., Tokyo, Japan) at the final concentration of 10%, 100 U/ml penicillin and 100 μg/ml streptomycin (NACALAI TESQUE, INC., Kyoto, Japan)).

Secretome-collecting filter (for enrichment of culture supernatant): Amicon Ultra-15 Centrifugal Filters Ultracel-3K (Millipore, Billerica, Mass.).

Protein preparation buffer: modified RIPA buffer (50 mM Tris-HCl (pH 7.4), 150 mM NaCl, 0.25% sodium deoxycholate, 0.1% SDS, 1% NP-40, 1 mM EDTA, 5% glycerol); and SDS sample buffer (60 mM Tris-HCl (pH 6.8), 5% 2-mercaptoethanol, 2% SDS, 0.10% BPB, 25% glycerol).

Note that final concentrations in the culture medium are provided in the above. Also, for preparing samples, 2× modified RIPA buffer (i.e. two-fold concentration), and 5×SDS sample buffer (i.e. five-fold concentration) were used.

The cell culture schedule was as shown in FIG. 1.

(Day −1)

UE7T-13 cells were seeded on each culture dish with a diameter of 10 cm such that the cell count in each dish was $9.0 \times 10^3$ cells/cm$^2$. The number of the culture dishes prepared was 6.

(Day 0)

The next day of seeding, IC-2 was added to 3 out of the 6 culture dishes prepared above by exchanging the culture medium with DMEM/10% FBS containing IC-2 at the final concentration of 15 µM. Cells in the remaining 3 culture dishes were treated with DMSO as control. Specifically, DMSO was added by completely exchanging the culture medium with DMEM/10% FBS containing DMSO at the final concentration of 0.1%.

(Day 3)

The culture medium was exchanged in the same manner as Day 0. For including MSC (i.e. chemical-untreated group), UE7T-13 cells were seeded on culture dishes with a diameter of 10 cm such that the cell count in each dish was $2.0 \times 10^4$ cells/cm$^2$. That is, the cells of chemical-untreated group, of which culture medium was collected for MSC, were seeded on 3 culture dishes with a diameter of 10 cm.

(Day 7)

The culture medium was completely exchanged with DMEM/0.05% FBS containing IC-2 at the final concentration of 15 µM. For the DMSO treatment control, the culture medium was completely exchanged with DMEM/0.05% FBS containing DMSO at the final concentration of 0.1%. For the MSC group, the culture medium was completely exchanged with DMEM/0.05% FBS.

(Day 9) Enrichment of Culture Supernatant and Preparation of Proteins:

(1) A 5 ml aliquot of culture medium was collected from the culture dishes and these aliquots were combined in one tube for each group. A 1 ml aliquot of the remaining culture medium was stored at −80° C. for ELISA assay. The samples were centrifuged to conduct the following enrichment, while DMEM/0.05% FBS was centrifuged in the same manner to provide a blank value.

(2) A 12 ml aliquot of the supernatant was transferred to an Amicon Ultra-15 Centrifugal Filter Unit and was centrifuged at 5,000 g for 60 to 90 min. The centrifugation period was adjusted as appropriate so that about 24-fold enrichment was achieved at the time of pipetting and measuring the liquid level.

(3) The absorbance of the enriched culture supernatant (secretome) was measured using a NanoDrop at 280 nm and the protein level was assayed. The blank culture medium and 2× modified RIPA buffer were added to adjust the protein concentration to 1.0 µg/µl. Then, a sonicator (BioRuptur manufactured by COSMO BIO, Tokyo, Japan) was used to perform the total 1 min and 4 cycles of sonication, each cycle including sonication at 200 W for 15 sec and a pause for 30 sec in ice bath. Then, 5×SDS sample buffer was added to adjust the protein concentration to 0.8 µg/µl. Finally, a block incubator (IKA, Staufen, Germany) was used for heat denaturing at 98° C. for 5 min.

Example 2

Western Blotting

For MMP-1 assay, samples containing 2.4 µg of protein were applied to the respective wells of 10% SDS polyacrylamide gel. For MMP-2, MMP-13 and MMP-14 assays, samples containing 10 µg of protein were applied to the respective wells of 10% SDS polyacrylamide gel. For thioredoxin assay, samples containing 10 µg of protein were applied to the respective wells of 15% SDS polyacrylamide gel. Each gel was electrophoresed at 20 mA for 80 min in a running buffer (25 mM Tris, 192 mM glycine, 0.1% SDS (all from NACALAI TESQUE, INC.)). Then, the gels were equilibrated by shaking for 5 min in a suitable volume of transfer buffer (25 mM Tris, 192 mM glycine). Then, proteins were transferred onto a 0.45-µm transfer membrane (Millipore Corp, Billerica, Mass.) using a Trans-Blot Turbo Transfer System (Bio-Rad) under conditions at 0.8 A and 25 V for 30 min. The transferred membranes were equilibrated by shaking for 5 min in a suitable volume of Tris-buffered saline (TBS)-T (0.1% Tween 20 (NACALAI TESQUE, INC.), 10 mM Tris, and 750 mM NaCl). Then, the membranes were stained by soaking in Ponceau S staining solution with shaking for 15 to 30 min until bands became clear. After washing 2 to 3 times in a suitable volume of TBS-T, the images of the membranes were taken for internal control. The blocking of the washed membranes was performed with 5% skim milk in TBS-T for MMP-1, MMP-2 and MMP-14; and with 3% BSA (NACALAI TESQUE, INC.) in TBS-T for MMP-13 and TRX at room temperature for 90 min. Then, the primary antibody reaction was performed by soaking the membrane in 5% skim milk/TBS-T containing 500-fold diluted rabbit polyclonal anti-MMP-1 antibody (Proteintech Group, Inc.); 5% skim milk/TBS-T containing 500-fold diluted rabbit polyclonal anti-MMP-2 antibody (Cell Signaling Technology); 1% BSA/TBS-T containing 500-fold diluted rabbit polyclonal anti-MMP-13 antibody (abcam); 5% skim milk/TBS-T containing 500-fold diluted rabbit polyclonal anti-MMP-14 antibody (abcam); or 1% BSA/TBS-T containing 1,000-fold diluted rabbit polyclonal anti-thioredoxin antibody (Cell Signaling Technology) with shaking overnight at 4° C.

After completion of the primary antibody reaction, the membranes were washed in a suitable volume of TBS-T for 10 min 3 times. Then, the secondary antibody reaction was performed by soaking the membrane in 5% BSA/TBS-T or 5% skim milk/TBS-T containing 3,000-fold diluted anti-rabbit HRP (GE Healthcare Life Sciences) with shaking at room temperature for 90 min. After completion of the secondary antibody reaction, the membranes were shaken in a suitable volume of TBS-T for 10 min 3 times. After that, 1 ml of ECL Prime liquid (GE Healthcare Life Sciences) was applied to each membrane of which chemiluminescence was detected with a LAS-4000 (Fujifilm Corporation, Tokyo, Japan).

Figure 2:
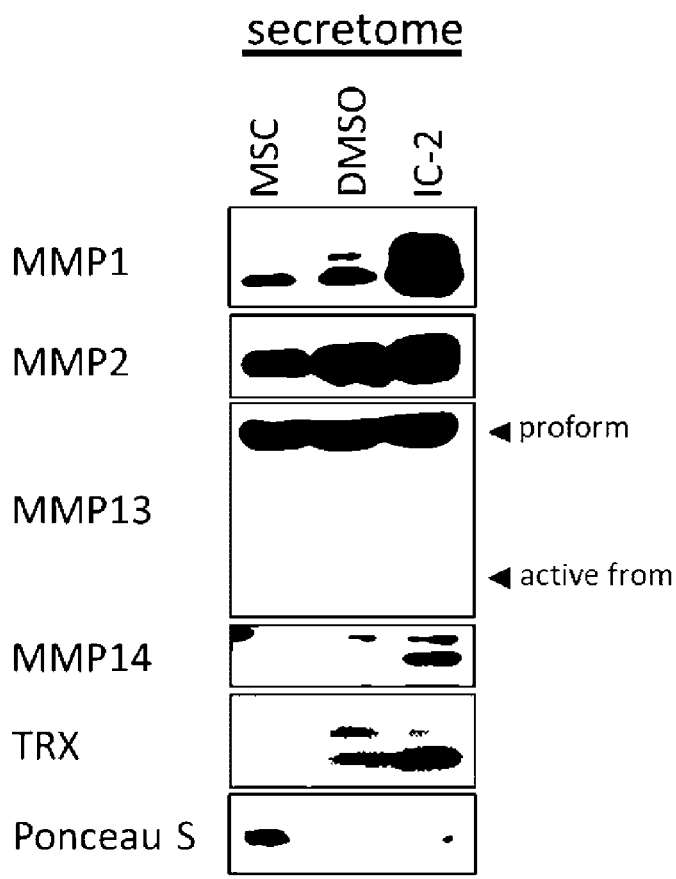
FIG. 2 is an image of Western blotting showing MMPs present in the composition of the invention. As explained in the Examples section below, as compared to the DMSO control group, MMP-1 was increased about 4.1-fold, MMP-2 was increased about 1.5-fold, MMP-13 (in an active form) was increased about 5.1-fold, and MMP-14 was increased about 2.1-fold in the IC-2 treatment group. This indicates that MMP-1 and MMP-13, which are collagenases, are specifically and markedly increased. Accordingly, the composition of the present invention has a higher capability of degrading collagens.

The results are shown in FIG. 2. By quantifying the Western blotting band intensities, the supernatant of the culture from the IC-2 treatment group was found to contain large amounts of MMP-1, MMP-2, MMP-13 and MMP-14 as compared to the supernatants of the MSC and DMSO groups.

By comparing the intensities of chemiluminescence, MMP-1 was increased about 4.1-fold, MMP-2 was increased about 1.5-fold, MMP-13 (active form) was increased about 2.1 fold and MMP-14 was increased about 5.1-fold in the IC-2 treatment group as compared to those of the DMSO control group.

Example 3

ELISA

The aliquots of culture supernatants collected at Day 9 for ELISA assay were used to determine the production of thioredoxin by ELISA. The frozen culture supernatants were thawed on ice, and then centrifuged at 1,000 g for 20 min at 4° C. to recover the supernatants. A Human TXN/Thioredoxin/TRX ELISA Kit (Sandwich ELISA) (LSBio) was used in accordance with the manufacturer's instructions. Briefly, serial dilutions of calibrator standard (i.e. 10000, 5000, 2500, 1250, 625, 312.5, 156.3, 78.15 and 0 pg/ml) were prepared by using the standard sample included in the kit. Then, 100 µl of the above standard or sample solution was placed in a well of the 96-well plate of the kit in duplicate. After incubating the plate at 37° C. for 90 min, the sample and standard solutions were removed from the wells by aspiration, followed by addition of 100 µl of 1× Detection Antibody and incubation at 37° C. for 60 min. After removing the reaction solutions from the wells by aspiration, the wells were washed 3 times with 150 µl of 1×PBS. Then, 100 µl of 1×ABC complex was added to the wells, followed by incubation at 37° C. for 30 min. After removing the reaction solutions from the wells by aspiration, the wells were washed 5 times with 150 µl of 1×PBS. Thereafter, 90 µl of TMB Substrate was added to the wells, followed by incubation at 37° C. for 20 min. Then, 100 µl of Stop Solution was added to the wells. The absorbance at 450 nm was measured using a microplate reader (Tecan Group Ltd). The content of thioredoxin in the culture supernatants was calculated from the absorbance using the calibration curve.

Figure 3:
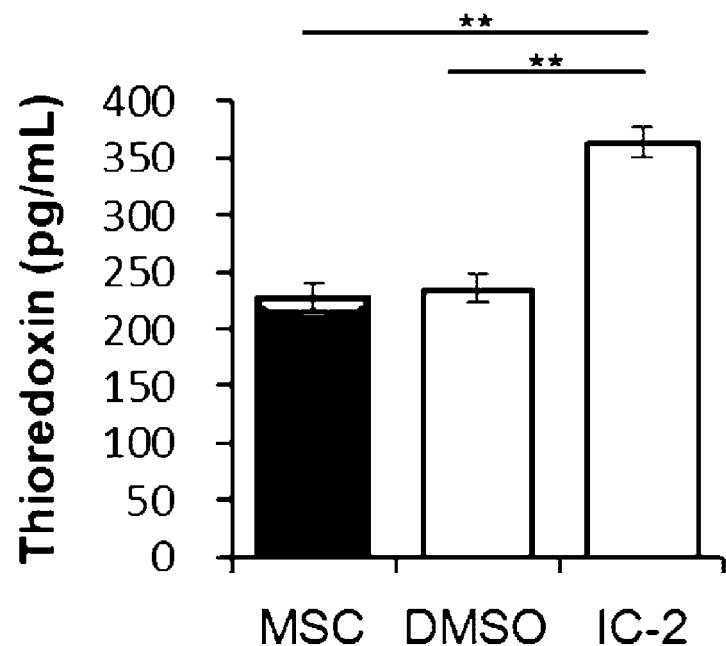
FIG. 3 shows a measurement of TRX activity by ELISA. The level of production was found to be 1.5-fold higher.

The results are shown in FIG. 3. The results of the ELISA shows that the production of thioredoxin increased 1.5-fold.

INDUSTRIAL APPLICABILITY

The composition for inhibiting fibrosis, the cell sheet having a high fibrosis inhibitory effect and the cell having fibrosis inhibitory activity according to the present invention can be used for regenerative medicine, etc., and are therefore applicable to the fields of, for instance, pharmaceutical industry.

The invention claimed is:

1. A method of producing a composition having high fibrosis inhibitory effect comprising the steps of:
   i) culturing bone marrow mononuclear cells or mesenchymal stem cells in a culture medium containing IC-2 or an analogous compound thereof for at least 9 days, characterized in that the concentration of IC-2 or the analogous compound thereof is maintained throughout the cultivation;
   ii) collecting cultured cells, secreted products of the cells or both from the culture obtained in the step i); and
   iii) recovering proteins from the cultured cells, the secreted products of the cells or the both collected in the step ii)
   wherein said composition comprises MMP-1, MMP-14, MMP-2, MMP-13, and thioredoxin (TRX).

2. The method according to claim 1, wherein the compound used in the step of culturing bone marrow mononuclear cells or mesenchymal stem cells in the culture medium containing IC-2 or the analogous compound thereof is represented by the following formula (1):

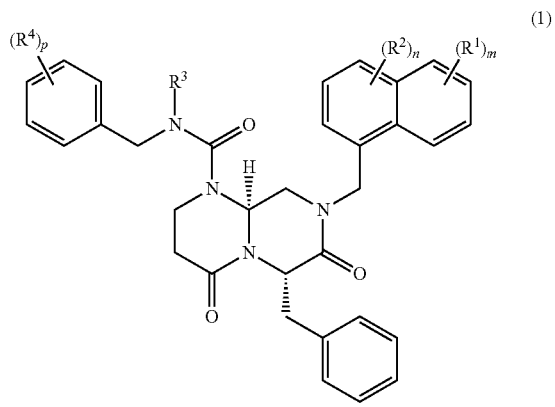

wherein $R^1$, $R^2$ and $R^4$ are the same or different and each represents H, halogen, nitro, cyano, OH, optionally substituted C1-C6 alkyl, optionally substituted C2-C6 alkenyl, optionally substituted C1-C6 alkoxy, aryl or heteroaryl;
$R^3$ is H, optionally substituted C1-C6 alkyl or optionally substituted C2-C6 alkenyl;
m is an integer from 1 to 4;
n is an integer from 1 to 3; and
p is an integer from 1 to 5,
provided that N-[(5-methyl-2-furyl)methylideneamino]-2-phenoxy-benzamide is excluded.

3. A method of producing a cell sheet having high fibrosis inhibitory effect comprising the steps of:
   i) culturing mesenchymal stem cells in a culture medium containing IC-2 or an analogous compound thereof for at least 9 days, characterized in that the concentration of IC-2 or the analogous thereof is maintained throughout the cultivation; and
   ii) collecting a cell sheet containing the mesenchymal stem cells and secreted products of said cells generated in the step i)
   wherein said cell sheet comprises MMP-1, MMP-14, MMP-2, MMP-13, and thioredoxin (TRX).

4. The method according to claim 3, wherein IC-2 or the analogous compound thereof is represented by the following formula (1):

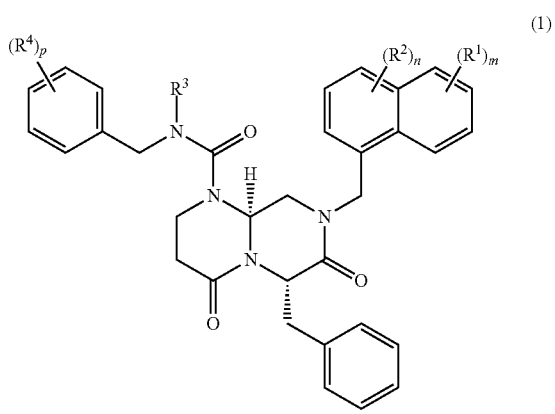

wherein $R^1$, $R^2$ and $R^4$ are the same or different and each represents H, halogen, nitro, cyano, OH, optionally substituted C1-C6 alkyl, optionally substituted C2-C6 alkenyl, optionally substituted C1-C6 alkoxy, aryl or heteroaryl;

$R^3$ is H, optionally substituted C1-C6 alkyl or optionally substituted C2-C6 alkenyl;

m is an integer from 1 to 4;

n is an integer from 1 to 3; and p is an integer from 1 to 5, provided that N-[(5-methyl-2-furyl)methylideneamino]-2-phenoxy-benzamide is excluded.

5. A method for increasing production of a fibrosis inhibitor by a mesenchymal stem cell comprising culturing bone marrow mononuclear cells or mesenchymal stem cells in a culture medium containing IC-2 or an analogous compound thereof for at least 9 days, characterized in that the concentration of IC-2 or the analogous compound thereof is maintained throughout the cultivation, wherein the fibrosis inhibitor is selected from the group consisting of MMP-1, MMP-14, MMP-2, MMP-13, thioredoxin (TRX), and a combination thereof.

6. The method according to claim 5, wherein IC-2 or the analogous compound thereof is represented by the following formula (1):

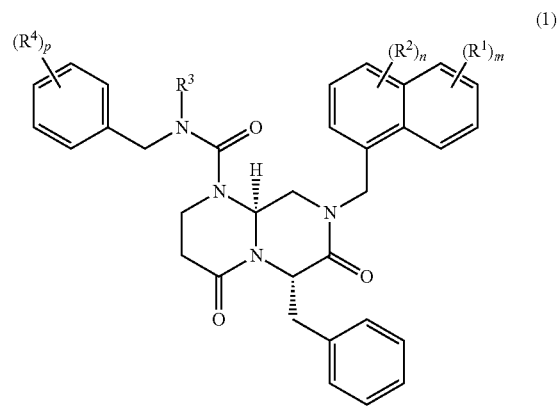

wherein $R^1$, $R^2$ and $R^4$ are the same or different and each represents H, halogen, nitro, cyano, OH, optionally substituted C1-C6 alkyl, optionally substituted C2-C6 alkenyl, optionally substituted C1-C6 alkoxy, aryl or heteroaryl;

$R^3$ is H, optionally substituted C1-C6 alkyl or optionally substituted C2-C6 alkenyl;

m is an integer from 1 to 4;

n is an integer from 1 to 3; and p is an integer from 1 to 5, provided that N-[(5-methyl-2-furyl)methylideneamino]-2-phenoxy-benzamide is excluded.

* * * * *